United States Patent
Lorence et al.

(10) Patent No.: US 9,844,574 B2
(45) Date of Patent: *Dec. 19, 2017

(54) CANCER TREATMENT USING VIRUSES AND CAMPTOTHECINS

(71) Applicant: Wellstat Biologics Corporation, Gaithersburg, MD (US)

(72) Inventors: Robert M Lorence, Bethesda, MD (US); Michael Scot Roberts, Myersville, MD (US)

(73) Assignee: Wellstat Biologics Corporation, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/195,200

(22) Filed: Jun. 28, 2016

(65) Prior Publication Data

US 2016/0303175 A1    Oct. 20, 2016

Related U.S. Application Data

(63) Continuation of application No. 14/076,485, filed on Nov. 11, 2013, now abandoned, which is a continuation of application No. 11/568,228, filed as application No. PCT/US2005/014144 on Apr. 26, 2005, now abandoned.

(60) Provisional application No. 60/565,631, filed on Apr. 27, 2004.

(51) Int. Cl.
*A61K 35/768* (2015.01)
*A61K 31/4745* (2006.01)
*A61K 45/06* (2006.01)
*A61K 39/395* (2006.01)

(52) U.S. Cl.
CPC ........ *A61K 35/768* (2013.01); *A61K 31/4745* (2013.01); *A61K 39/39558* (2013.01); *A61K 45/06* (2013.01); *C12N 2760/18132* (2013.01)

(58) Field of Classification Search
None
See application file for complete search history.

(56) References Cited

U.S. PATENT DOCUMENTS

| | | | |
|---|---|---|---|
| 4,604,463 A | 8/1986 | Miyasaka et al. | |
| 5,004,758 A | 4/1991 | Boehm et al. | |
| 6,403,569 B1 | 6/2002 | Achterrath | |
| 6,428,968 B1 | 8/2002 | Molnar-Kimber et al. | |
| 7,056,689 B1 | 6/2006 | Lorence et al. | |
| 7,223,389 B2 | 5/2007 | Zakay-Rones et al. | |
| 7,279,333 B2 | 10/2007 | Kaneda | |
| 7,427,395 B2 | 9/2008 | Yamamoto et al. | |
| 7,736,640 B2 | 6/2010 | Lorence et al. | |
| 7,767,200 B2 | 8/2010 | Lorence et al. | |
| 2002/0071832 A1 | 6/2002 | Fong et al. | |
| 2002/0168344 A1 | 11/2002 | Coffey et al. | |
| 2003/0044384 A1 | 3/2003 | Roberts et al. | |
| 2003/0068307 A1 | 4/2003 | Yu et al. | |
| 2004/0253272 A1 | 12/2004 | Kaneda | |
| 2005/0147591 A1 | 7/2005 | Hallahan et al. | |
| 2006/0165656 A1 | 7/2006 | Yamamoto et al. | |
| 2007/0128170 A1 | 6/2007 | Zakay-Rones et al. | |
| 2007/0207149 A1 | 9/2007 | Lorence et al. | |

FOREIGN PATENT DOCUMENTS

| | | |
|---|---|---|
| WO | 1994/25627 A1 | 11/1994 |
| WO | 1997/025332 | 7/1997 |
| WO | 1997/028164 | 8/1997 |
| WO | 1997/016454 | 9/1997 |
| WO | 1998/035969 | 8/1998 |
| WO | 1999/005103 | 4/1999 |
| WO | 1999/017804 | 4/1999 |
| WO | 1999/017805 | 4/1999 |
| WO | 1999/25860 A1 | 5/1999 |
| WO | 2000/07605 | 2/2000 |
| WO | 2000/053607 | 9/2000 |
| WO | 2000/62735 A2 | 10/2000 |
| WO | 2001/064194 | 9/2001 |
| WO | 2001/70275 A2 | 9/2001 |
| WO | 2001/076597 | 10/2001 |
| WO | 2003/022202 | 3/2003 |
| WO | 2003/086471 | 10/2003 |
| WO | 2003/093274 | 11/2003 |
| WO | 2003/101406 | 12/2003 |
| WO | 2003/101996 | 12/2003 |
| WO | 2003/101998 | 12/2003 |
| WO | 2004/000209 A2 | 12/2003 |
| WO | 2004/012661 | 2/2004 |
| WO | 2004/039406 A1 | 5/2004 |

(Continued)

OTHER PUBLICATIONS

Poster# 5428, AACR meeting, Apr. 6-10, 2002 in San Francisco.*

(Continued)

*Primary Examiner* — Nianxiang Zou
(74) *Attorney, Agent, or Firm* — Lewis J. Kreisler

(57) ABSTRACT

Mammalian subjects having a neoplasm are treated with a virus and a camptothecin compound, for example irinotecan or topotecan. The virus is selected from the group consisting of a Newcastle disease virus, a measles virus, a vesicular stomatitis virus, an influenza virus, a Sindbis virus, a picornavirus, and a myxoma virus. The treatment can also include administration of a monoclonal antibody against epidermal growth factor receptor, for example cetuximab.

13 Claims, No Drawings

(56) References Cited

FOREIGN PATENT DOCUMENTS

| | | |
|---|---|---|
| WO | 2005/113013 | 12/2005 |
| WO | 2005/115391 | 12/2005 |

OTHER PUBLICATIONS

Ramanathan et al. (Semin Oncol. Aug. 1997;24(4):440-54).*
Cats (J Gastroenterol Suppl. 2003;(239):78-86).*
Slichenmyer et al. (Cancer Treat Res. 1995;78:29-43).*
Lorence et al., "Systemic therapy of human tumor xenografts using PV701, an oncolytic strain of Newcastle Disease Virus, in combination with a cytotoxic drug demonstrates at least additive antitumor responses", Poster #5428, AACR meeting, San Francisco, 2002.
Ramanathan RK, Belani CR, "Chemotherapy for advanced non-small cell lung cancer: past, present, and future", Semin Oncol. Aug. 1997; 24(4): 440-54.
Jonsson et al., "Differential activity of topotecan, irinotecan and SN-38 in fresh humann tumour cells but not in cell lines", Eur. J. Cancer. 36(16): 2120-7, Oct. 2000.
Lam et al., "Safety and Clinical Usage of Newcastle Disease Virus in Cancer Therapy", J. Biomed. and Biotechnol. vol. 2011: Article ID 718710, 13 pages, 2011.
Cats A., "New developments in systemic chemotherapy in advanced colorectal cancer", Scand J Gastroenterol Suppl. (2003) 239:78-86.
Slichenmyer et al., "Recent clinical advances with camptothecin analogues", Cancer Treat. Res. 78: 29-43, 1995.
Pecora, et al., "Phase I Trial of Intravenous Administration of PV701, an Oncolytic Virus, in Patients With Advanced Solid Cancers" J. Clin. Oncol. (2002) 20(9): 2251-2266.
Hasenburg, et al., "Thymidine kinase gene therapy with concomitant topotecan chemotherapy for recurrent ovarian aancer" Cancer Gene Therapy (2000) 7(6): 839-844.
Robert M. Lorence, "Continuing the Interaction Between Non-Clinical and Clinical Studies" slides presented Mar. 12, 2005 at Oncolytic Viruses meeting in Banff, Alberta, Canada; slide #25 on p. 5.
Garcia-Carbonero, et al., "Minireview: Current Perspectives on the Clinical Expeience, Pharmacology, and Continued Development of the Camptothecins" Clin. Cancer Research (Mar. 2002) 8: 641-661.
Kelly, et al., "Camptothecin: an Inhibitor of Influenza Virus Replication", J. Gen. Virol (1974) 25: 427-432.
Horwitz, et al., "Antiviral Action of Camptothecin", Antimicrobial Agents and Chemotherapy, (1972) 2(5): 395-401.
Mendelsohn, et al., "Status of Epidermal Growth Factor Receptor Anatgonists in the Biology and Treatment of Cancer", Journal of Clinical Oncology, (2003) 21(14): 2787-2799.
Alexander, "Chapter 27: Newcastle Disease" A Laboratory Manual for the Isolation and Identification of Avian Pathogens, 3rd Edition, Kendal/Hunt, 1989: 114-120.
Meck, et al., "A Virus-directed Enzyme Prodrug Therapy Approach to Purging Neuroblastoma Cells from Hematopoietic Cells Using Adenovirus Encoding Rabbit Carboxylesterase and CPT-11", Cancer Research, (2001) 61: 5083-5089.
Pizzolato, et al., "The Camptothecins", The Lancet, (2003) 361: 2235-2242.
Kim, "Virotherapy for Cancer: Current Status, Hurdles, and Future Directions", Cancer Gene Therapy, (2002) 9: 959-960.
Koehne, et al., "Current Review of Chemotherapy for Colorectal Cancer: A European Perspective", Biotherapy, 17(4): 368-378, Jul. 2003.
Saji et al. "Anti-HER2 Antibody, Anti-EGFR Antibody, Anti-VEGF Antibody", Surgery Frontier, 10(2): 75-82, 2003. (including English translation of the title and summary section).
Omura, "Treatment of Metastatic Liver Carcinoma: Chemotherapy and Immunotherapy", Journal of Japanese Surgical Society, 104(10): 730-734, 2003.
You, et al., "Future Directions: Oncolytic Viruses", Clinical Lung Cancer, 5(4): 226-230, Jan. 2004.
Heideman, "Gene Therapy and Virotherapy of Gastric Cancer: Preclinical Results and Clinical Development", Digestive Diseases, 22(4):374-379, 2004.
Smith, et al., "Oncolytic viruses as novel anticancer agents: turning one scourge against another", Expert Opinion on Investigational Drug, 9(2): 311-327, 2000.
Stathopoulos, et al., Leucovorin, 5-fluorouracil, irrinotecan, oxaliplatin combination in pretreated advanced colorectal aancer patients, ASCO Annual Meeting, Proc Am Soc Clin Oncology 22: Jun. 2003. (Abstract 1213).
Vanhoefer, et al., "Irinotecan in the Treatment of Colorectal Cancer: Clinical Overview", J. Clin. Oncology, 19(5): 1501-1518, Mar. 2001.
Hoff, et al., "The Evolution of Fluoropyrimidine Therapy: From Intravenous to Oral" The Oncologist, 6(4):3-11, 2001.
Teufel, et al., "Irinotecan plus folinic acid/continuous 5-fluorouracil as simplified bimonthly FOLFIRI regimen for first-line therapy of metastatic colorectal cancer", BMC Cancer, 4(38): 1-8, Jul. 2004.
Tournigand, et al., "FOLFIRI followed by FOLFOX6 or the reverse sequence in advanced colorectal cancer: A randomized GERCOR study", J Clin Oncol, 22(2): 229-237, Epub, Dec. 2003.
Andre, et al., "CPT-11 (Irinotecan) Addition to Bimonthly, High-dose Leucovorin and Bolus and Continuous-infusion 5-Fluorouracil (FOLFIRI) for Pretreated Metastatic Colorectal Caner", European Journal of Cancer, 35(9): 1343-1347, 1999.
Bouche, et al., "Randomized Multicenter Phase II Trial of a Biweekly Regimen of Fluorouracil and Leucovorin (LV5FU2), LV5FU2 Plus Cisplatin, or LV5FU2 Plus Irinotecan in Patients with Previously Untreated Metastatic Gastric Caner: A Federation Francophone de Cancerologie Digestive Group Study—FFCD 9803", Journal of Clinical Oncology, 22(21): 4319-4328, Nov. 2004.
Ducreux, et al., "Irinotecan Combined with Bolus Fluorouracil, Continuous Infusion Fluorouracil, and High-Dose Leucovorin Every Two Weeks (LV5FU2 Regimen): A Clinical Dose—Finding and Pharmacokinetic Study in Patients with Pretreated Metastatic Colorectal Cancer", Journal of Clinical Oncology, (1999), 17(9): 2901-2908.
Goto, et al, "Phase I/II study of irinotecan, 5-fluorouracil, and l-Leucovorin combination therapy (modified Saltz regimen) in patients with metastatic colorectal cancer", Int. J. Clinical Oncology, 9: 364-368, Oct. 2004.
Petty, et al., "Novel Fluoropyrimidines: Improving the Efficacy and Tolerability of Cytotoxic Therapy", Current Cancer Drug Targets, 4: 191-204, Mar. 2004.
Lamont, et al., "The Oral Fluoropyrimidines in Cancer Chemotherapy", Clinical Cancer Research, 5: 2289-2296,1999.
Rustum, et al., "Rationale for Treatment Design: Biochemical Modulation of 5-Fluorouracil by Leucovorin", The Cancer Journal from Scientific American, 4(1): 12-18, 1998.
Vincent, et al., "Which 5-Fluorouracil regimen?—the great debate", Anti-Cancer Drugs, 10: 337-354, 1999.
Saltz, et al., "Phase I Clinical and Pharmacokinetic Study of Irinotecan, Fluorouracil, and Leucovorin in Patients with Advanced Solid Tumors", Journal of Clinical Oncology, 14(11): 2959-2967, 1996.
Jolivet, "Role of Leucovorin Dosing and Administration Schedule", European Journal of Cancer, 31A(7/8): 1311-1315, 1995.
Lorence, et al., "Overview of phase I studies of intravenous administration of PV701 an oncolytic virus", Current Opinion in Molecular Therapeutics, 5(6), 618-624, Dec. 2003.
Reichard, et al., "Newcastle disease virus selectively kills human tumor cells", J Surg Res. (May 1992) 52(5):448-53.
Ex parte Feldmann et al., Decision on Appeal, Appeal No. 2002-0253 (Bd. Pat. App. Int. Mar. 2003).
Negoro et al. "A phase II study of CPT-11, a camptothecin derivative, in patients with primary lung cancer. CPT-11 Cooperative Group Study" Gan to Kagaku Ryoho (Japanese Journal of Cancer & Chemotherapy) (1991) 18:1013-1019. (Abstract only).
Shah et al. "Oncolytic viruses: clinical applications as vectors for the treatment of malignant gliomas" J Neurooncol. Dec. 2003;65:203-26.
Ring, "Cytolytic viruses as potential anti-cancer agents" J Gen Virol. (2002) 83:491-502.

(56) References Cited

OTHER PUBLICATIONS

Hasenburg et al. "Thymidine kinase gene therapy with concomitant topotecan chemotherapy for recurrent ovarian cancer" Cancer Gene Ther. (2000) 7(6):839-44.
Heise et al. "ONYX-015, an E1B gene-attenuated adenovirus, causes tumor-specific cytolysis and antitumoral efficacy that can be augmented by standard chemotherapeutic agents" Nature Medicine (1997) 3(6):639-645.
Chahlavi et al. "Replication-competent Herpes Simplex virus vector G207 and cisplatin combination therapy for head and neck squamous cell carcinoma" (1999) Neoplasia 1(2):162-169.
Wildner et al. "Therapy of colon cancer with oncolytic adenovirus is enhanced by the addition of herpes simplex virus-thymidine kinase" (1999) Cancer Research 59:410-413.
U.S. Appl. No. 11/913,362, Office Action dated Mar. 19, 2009.
Atherton and Burke, "Interferon Induction by viruses and polynucleotides: a differential effect of camptothecin", (1975) J. Gen. Virol. 29:297-304.
Phuangsab et al., "Newcastle disease virus therapy of human tumor xenografts: antitumor effects of local or systemic administration", Cancer Lett. Oct. 22, 2001; 172(1):27-36.
Prewett et al., "Enhanced antitumor activity of anti-epidermal growth factor receptor monoclonal antibody IMC-C225 in combination with irinotecan (CPT-11) against human colorectal tumor xenografts", Clin Cancer Res. May 2002; 8(5):994-1003.
Nemunaitis et al., "Plot trial of intravenous infusion of a replication-selective adenovirus (ONYX-015) in combination with chemotherapy or IL-2 treatment in refractory cancer patients", Cancer Gene Ther. May 2003; 10(5)341-52.

* cited by examiner

CANCER TREATMENT USING VIRUSES AND CAMPTOTHECINS

BACKGROUND OF THE INVENTION

Coadministration of oncolytic viruses with other chemotherapeutic agents is disclosed in WO 00/62735 (pages 35-36). See Kirn D (Cancer Gene Ther 2002; 9:959-960; Virotherapy for cancer: current status, hurdles and future directions) and Bell J C et al. (Cur Gene Ther 2002, 2:243-254; Oncolytic viruses: programmable tumour hunters) for recent reviews on anti-cancer virus therapy Improvements in efficacy using such virus therapies are important to the field and getting approval and widespread use of the approach. Specifically, a drug which shows supra-additive efficacy with a virus would be most advantageous.

The use of camptothecins as anticancer agents is reviewed in Garcia-Carbonero, et al., Clin. Cancer Res. (March 2002) 8: 641-661; and in Pizzolato J F and Saltz L B, The camptothecins. Lancet 2003 361:2235-42. Camptothecins have antitumor activity based on their binding to and inhibition of topoisomerase I, a nuclear enzyme which reduces torsional stress during DNA replication and which has an important role in DNA replication. Topotecan and irinotecan are the two camptothecins have been approved for clinical use by the US Food and Drug Administration (FDA). Other camptothecins are in development as cancer therapeutics (Ulukan and Swaan, (Campothecins: a review of their chemotherapeutic potential. Drugs, 2002, 62:2039-57); and Garcia-Carbonero and Supko, 2002).

The treatment of cancers using certain mutant herpes viruses in combination with any of numerous anticancer agents, including irinotecan and topotecan, is disclosed in U.S. Patent Publication No. 2002/0071832 (Fong, et al.), paragraphs 7 and 40. Methods of treating neoplasias using target cell-specific adenoviral vectors in combination with antineoplastic agents, including irinotecan or topotecan, are disclosed in U.S. Patent Publication No. 2003/0068307 (Yu, et al.) page 13. See also Nemunaitis, et al., Cancer Gene Ther. (2003) 10(5): 341-352; and Meck, et al., Cancer Res. (2001) 61(13): 5083-5089. Combined use of irinotecan and cetuximab was approved in February 2004 by the U.S. FDA to treat colorectal cancer.

SUMMARY OF THE INVENTION

This invention provides a method for treating a mammalian subject having a neoplasm, comprising administering to the subject a virus and a camptothecin compound in a combined amount effective to treat the subject; wherein the virus is selected from the group consisting of a Newcastle disease virus, a measles virus, a vesicular stomatitis virus, an influenza virus, a Sindbis virus, a picornavirus, and a myxoma virus. In an embodiment of this invention the treatment further comprises administering to the subject a monoclonal antibody against epidermal growth factor receptor in an amount effective, in combination with the virus and the camptothecin compound, to treat the subject.

This invention provides for the use of a virus and/or a camptothecin compound in the manufacture of a medicament for treating, in combination with the other ingredient mentioned, a subject having a neoplasm; wherein the virus is selected from the group consisting of a Newcastle disease virus, a measles virus, a vesicular stomatitis virus, an influenza virus, a Sindbis virus, a picornavirus, and a myxoma virus. This invention also provides the use of a monoclonal antibody against epidermal growth factor receptor in the manufacture of a medicament for treating, in combination with a virus as mentioned above and a camptothecin compound, a subject having a neoplasm.

This invention is based on the finding that anti-cancer viruses and camptothecins in combination are effective against neoplastic cells. To illustrate, a mesogenic strain of Newcastle disease virus and irinotecan, a camptothecin compound, have demonstrated a greater than additive level of in vivo antitumor activity, as shown in the examples.

DETAILED DESCRIPTION OF THE INVENTION

As used herein the transitional term "comprising" is open-ended. A claim utilizing this term can contain elements in addition to those recited in such claim. Thus, for example, the claims can read on treatment regimens that also include other therapeutic agents or therapeutic virus doses not specifically recited therein, as long as the recited elements or their equivalent are present.

As used herein "NDV" is an abbreviation for Newcastle Disease Virus. As used herein "DLT" is an abbreviation for dose limiting toxicity. As used herein the term "plaque-forming unit" (PFU) means one infectious virus particle. As used herein "BPFU" means billion PFUs. As used herein "PP" means plaque-purified. Thus, for example PPMK107 means plaque-purified Newcastle Disease virus strain MK107. As used herein "PFU/m$^2$", which is a standard unit for expressing dosages, means PFUs per square meter of patient surface area. As used herein the term "replication-competent" virus refers to a virus that produces infectious progeny in cancer cells.

In an embodiment of this invention the virus is replication-competent.

In accordance with this invention, when the virus is a Newcastle Disease Virus it can be of low (lentogenic), moderate (mesogenic) or high (velogenic) virulence. The level of virulence is determined in accordance with the Mean Death Time in Eggs (MDT) test. (Alexander, "Chapter 27: Newcastle Disease" in Laboratory Manual for the Isolation and Identification of Avian Pathogens, 3$^{rd}$ ed., Purchase, et al. eds. (Kendall/Hunt, Iowa), page 117.) Viruses are classified by the MDT test as lentogenic (MDT>90 hours); mesogenic (MDT from 60-90 hours); and velogenic (MDT<60 hours). Mesogenic NDV is currently preferred.

In accordance with this invention, any conventional route or technique for administering viruses to a subject can be utilized. For examples of routes of administration refer to WO 00/62735. In one embodiment of this invention, the virus is administered systemically, for example intravenously. For intravenous administration of a therapeutic virus in accordance with this invention, preferably the virus is a mesogenic strain of Newcastle Disease Virus. In a preferred embodiment of this invention, from $12 \times 10^9$ to $120 \times 10^9$ PFU/m$^2$ per dose of a mesogenic strain of Newcastle Disease virus is administered intravenously to a human subject, more preferably from $12 \times 10^9$ to $48 \times 10^9$ PFU/m$^2$ per dose. As used herein "mg/m$^2$" means milligrams per square meter of patient surface area.

In embodiments of this invention the picornavirus is a poliovirus, an echovirus, or a coxsackievirus. Examples of coxsackieviruses that are suitable in accordance with this invention include the following types: A21, A13, A15 and A18. Examples of suitable echoviruses include echovirus type 1.

As used herein the term "camptothecin compound" means that class of compounds considered to be camptothecins, camptothecin analogs, camptothecin derivatives or camptothecin conjugates. These compounds are based on the characteristic five-ring backbone of camptothecin:

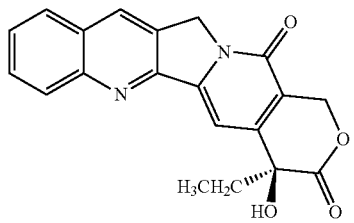

In accordance with this invention any camptothecin compound can be utilized. Examples of camptothecin compounds include irinotecan (CAMPTOSAR; 7-ethyl-10-[4-(1-piperidino)-1-piperidino]-carbonyloxycamptothecin), topotecan (HYCAMPTIN; (S)-9-N,N-dimethylaminoethyl-10-hydroxycamptothecin), 9-aminocamptothecin (9-amino-20(S)-camptothecin), 9-nitrocamptothecin (also called rubitecan), lurtotecan (7-(4-methylpiperazinomethylene)-10,11-ethylenedioxy-20(S)-camptothecin), exatecan, karenitecin, and a homocamptothecin. The structures and clinical information for some camptothecin compounds can be found in Garcia-Carbonero, et al., Clin. Cancer Res. (March 2002) 8: 641-661. Examples of camptothecin compounds can also be found in U.S. Pat. Nos. 4,604,463, 6,403,569, and 5,004,758, and in WO 2004/012661, WO 2003/101998, WO 2003/101996, WO 2003/101406, WO 2003/093274, WO 2003/086471, WO 01/76597, WO 01/64194, WO 00/70275, WO 00/53607, WO 99/17805, WO 99/17804, WO 99/05103, WO 98/35969, WO 97/28164, WO 97/25332, WO 97/16454, the contents of all of which are incorporated herein by reference.

In accordance with the combination therapy of this invention the camptothecin compound can be administered from one month before administration of the virus until one month after administration of the virus. In more specific embodiments the camptothecin compound and the virus are administered to the subject within a single twenty-four hour period; or the camptothecin compound is administered from twenty-four hours to one month, preferably from twenty-four hours to one week, before administration of the virus; or the camptothecin compound is administered to the subject from twenty-four hours to one month, preferably from twenty-four hours to one week, after administration of the virus. The dosing and administration techniques and schedules for camptothecins and anti-cancer viruses are known in the art (See, e.g. Garcia-Carbonero, et al.; WO 00/62735; WO 2004/000209; and Pecora, et al., J. Clin. Oncol. (2002) 20(9): 2251-2266), and their optimization for a specific patient is within the ability of the skilled clinician. Irinotecan is usually administered to human patients in a dosage amount of from 62.5 to 125 mg/m$^2$ four times per week, or more preferably 80 to 125 mg/m$^2$ four times per week; or from 300 to 350 mg/m$^2$ once every three weeks, or more preferably 300 to 350 mg/m$^2$ once every three weeks. In accordance with this invention any antibody against epidermal growth factor receptor can be utilized. Chimeric and humanized monoclonal antibodies are preferred. Examples of suitable anti-EGF antibodies include cetuximab (tradename: ERBITUX), ABX-EGF, MDX-447, h-R3, and EMD-7200 (see Mendelsohn J and Baselga J, "Status of epidermal growth factor receptor antagonists in the biology and treatment of cancer", 2004 J Clin Oncol 21:2787-2799). Cetuximab is preferably administered to human patients intravenously, and is usually administered in an initial intravenous infusion of from 200 to 400 mg/m$^2$, followed approximately weekly thereafter by subsequent infusions of from 125 to 250 mg/m$^2$.

The subject that is treated in accordance with this invention can be either a human subject or a non-human mammalian subject. In accordance with this invention, any neoplasm can be treated, including but not limited to the following: rectal cancer, pelvic cancer, colon cancer, lung cancer, breast cancer, prostate cancer, glioblastoma, renal cancer, pancreatic cancer, head and neck cancer, endometrial cancer, neuroblastoma, carcinoid, melanoma, ovarian cancer, sarcoma, cancer of the gastro-esophageal junction, gastric cancer, esophageal cancer, liver cancer, and cervical cancer.

Although monitoring the treatment is not an essential aspect of the invention, there are techniques for measuring the therapeutic effects of the treatment. These include, measuring the size of the tumor after administration of the virus, and a decrease in tumor size is a positive result.

The invention will be better understood by reference to the following examples, which illustrate but do not limit the invention described herein. In the following examples 1 to 6, the NDV is a triple-plaque purified MK107, which is an attenuated (mesogenic) version of Newcastle Disease Virus, described more fully in International Patent Publication WO 00/62735, published Oct. 26, 2000 (Pro-Virus, Inc.). The entire content of WO 00/62735 is hereby incorporated herein by reference.

EXAMPLES

Example 1

NDV in Combination with Irinotecan

Athymic mice were injected subcutaneously with 10 million human HT1080 fibrosarcoma cells. Five days later when the subcutaneous tumors were approximately 100 mm$^3$ in size, groups of animals were treated intraperitoneally with irinotecan (25 mg/kg) or vehicle. Two days later animals were treated intravenously with either NDV (6×10$^6$ plaque forming units, PFU) or vehicle. The incidence of complete tumor regression (CR, 100% tumor reduction) was much higher in the group receiving both irinotecan and NDV (60%) than either irinotecan alone (30%) or NDV alone (0%); see Table 1.

TABLE 1

Treatment of tumor-bearing mice with irinotecan 2 days before treatment with NDV yields greater complete tumor responses than either agent alone.

| Treatment | Number of Mice | CR, % |
| --- | --- | --- |
| Irinotecan | 10 | 30% |
| NDV | 10 | 0% |
| Both Irinotecan and NDV | 10 | 60% |
| Vehicle Control | 10 | 0% |

Example 2

NDV in Combination with Irinotecan

Athymic mice were injected subcutaneously with 10 million human HT1080 fibrosarcoma cells. Seven days later when the subcutaneous tumors were approximately 125 mm³ in size, groups of animals were treated intraperitoneally with irinotecan (25 mg/kg) or vehicle and then approximately one hour later they were treated intravenously with either NDV (6×10⁶ plaque forming units, PFU) or vehicle. The incidence of complete tumor regression (CR, 100% tumor reduction) was much higher in the group receiving both irinotecan and NDV (90%) than either irinotecan alone (50%) or NDV alone (0%), see Table 2.

TABLE 2

Treatment of tumor bearing mice with irinotecan the same day as treatment with NDV yields greater complete tumor responses than either agent alone.

| Treatment | Number of Mice | CR, % |
|---|---|---|
| Irinotecan | 10 | 50% |
| NDV | 10 | 0% |
| Both Irinotecan and NDV | 10 | 90% |
| Vehicle Control | 10 | 0% |

Example 3

NDV in Combination with Irinotecan

Athymic mice were injected subcutaneously with 10 million human HT1080 fibrosarcoma cells. Seven days later when the subcutaneous tumors were approximately 387 mm³ in size, groups of animals were intravenously with either NDV (6×10⁶ plaque forming units, PFU) or vehicle. Two days later, the mice were then treated with treated intraperitoneally with irinotecan (25 mg/kg) or vehicle. The incidence of complete tumor regression (CR, 100% tumor reduction) was much higher in the group receiving both irinotecan and NDV (70%) than either irinotecan alone (10%) or NDV alone (0%), see Table 3.

TABLE 3

Treatment of tumor bearing mice with irinotecan two days after treatment with NDV yields greater complete tumor responses than either agent alone.

| Treatment | Number of Mice | CR, % |
|---|---|---|
| Irinotecan | 10 | 10% |
| NDV | 10 | 0% |
| Both Irinotecan and NDV | 10 | 70% |
| Vehicle Control | 10 | 0% |

Example 4

NDV in Combination with Weekly Dosing of Irinotecan

Cancer patients are treated with NDV followed by treatment with irinotecan. In each 3 week portion of the 6 week cycle, NDV treatment consist of six total intravenous treatments given at three times per week for two weeks followed by a one week rest period (see Table 4 below). The first dose of each cycle consists of 12 to 24 billion PFU/m² (administered over 3 hours for course 1 and over 1 hour for all other courses) followed by additional doses of between 24 to 48 billion PFU/m² (each dose administered over 1 hour). Irinotecan is given for four consecutive weeks on a weekly basis beginning during week 3 or 4 of cycle 1 followed by two weeks without irinotecan therapy (As an example, see Table 4 below). Additional 6 week courses (also termed cycles) of both NDV and irinotecan are given to the patients.

TABLE 4

Combination of treatment of NDV using irinotecan (80 to 125 mg/m²) given weekly ×4. Cycles of treatment are repeated every 6 weeks.

| Cycle | Week | NDV? | Irinotecan? |
|---|---|---|---|
| 1 | 1 | 3 doses/wk for two | No |
|   | 2 | weeks followed by 1 | No |
|   | 3 | week off | Yes, one dose over 90 minutes |
|   | 4 | 3 doses/wk for two | Yes, one dose over 90 minutes |
|   | 5 | weeks followed by 1 | Yes, one dose over 90 minutes |
|   | 6 | week off | Yes, one dose over 90 minutes |
| 2 | 1 | 3 doses/wk for two | No |
|   | 2 | weeks followed by 1 | No |
|   | 3 | week off | Yes, one dose over 90 minutes |
|   | 4 | 3 doses/wk for two | Yes, one dose over 90 minutes |
|   | 5 | weeks followed by 1 | Yes, one dose over 90 minutes |
|   | 6 | week off | Yes, one dose over 90 minutes |

Example 5

NDV in Combination Irinotecan Given Once Every 3 Weeks

Cancer patients are treated with NDV followed by treatment with irinotecan. NDV treatment consist of six total intravenous treatments given at three times per week for two weeks followed by a one week rest period (see Table 5 below). The first dose of six consists of 12 to 24 billion PFU/m² (administered over 3 hours for course 1 and over 1 hour for all other courses) followed by a additional doses of 24 to 48 billion PFU/m² (each dose administered over 1 hour). Patients begin their irinotecan therapy during week 3 and are given one dose every 3 weeks (See Table 5 below). Additional 3 week courses of both NDV and irinotecan are given to the patients.

TABLE 5

Combination of treatment of NDV using irinotecan given once every 3 wks. Cycles of treatment are repeated every 3 weeks.

| Cycle | Week | NDV? | Irinotecan? |
|---|---|---|---|
| 1 | 1 | 3 doses/wk for two | No |
|   | 2 | weeks followed by | No |
|   | 3 | 1 week off | Yes, one dose at 300 to 350 mg/m² over 30 minute intravenous infusion |
| 2 | 4 | 3 doses/wk for two | No |
|   | 5 | weeks followed by | No |
|   | 6 | 1 week off | Yes, one dose at 300 to 350 mg/m² over 30 minute intravenous infusion |

Example 6

NDV in Combination with Irinotecan and Cetuximab

Cancer patients are treated with both NDV and irinotecan as in examples 4 and 5, except that they additionally receive treatment with cetuximab [ERBITUX, a monoclonal antibody (mAb) against the epidermal growth factor receptor (EGFR)]. Cetuximab dosing begins on week 3 or week 4. The cetuximab dose is 200 to 400 mg/m² for the first intravenous (IV) infusion [administered as a 120 minute IV infusion (with a maximal infusion rate of 5 mL/min)] then 125 to 250 mg/m$^2$ [infused IV over 60 minutes] administered weekly thereafter. Some patients may also receive an initial test dose of cetuximab of 20 mg. Diphendydramine (50 mg IV) is commonly given to help lessen any infusion reactions due to cetuximab.

What is claimed is:

1. A method of treating a mammalian subject having a neoplasm, comprising administering to the subject a Newcastle disease virus and a camptothecin compound in a combined amount effective to treat the subject.

2. The method of claim 1, further comprising administering to the subject a monoclonal antibody against epidermal growth factor receptor in an amount effective, in combination with the virus and the camptothecin compound, to treat the subject.

3. The method of claim 2, wherein the monoclonal antibody is cetuximab.

4. The method of claim 1, wherein the virus is replication-competent.

5. The method of claim 1, wherein the virus is a mesogenic strain of Newcastle disease virus.

6. The method of claim 1, wherein the virus is administered intravenously.

7. The method of claim 1 wherein the camptothecin compound is selected from the group consisting of topotecan, 9-aminocamptothecin, exatecan, karenitecin, rubitecan, lurtotecan, and a homocamptothecin.

8. The method of claim 1, wherein the camptothecin compound is irinotecan.

9. The method of claim 1, wherein the camptothecin compound and the virus are administered to the subject within a single twenty-four hour period.

10. The method of claim 1, wherein the camptothecin compound is administered from twenty-four hours to one month before administration of the virus.

11. The method of claim 10, wherein the camptothecin compound is administered from twenty-four hours to one week before administration of the virus.

12. The method of claim 1, wherein the camptothecin compound is administered to the subject from twenty-four hours to one month after administration of the virus.

13. The method of claim 12, wherein the camptothecin compound is administered to the subject from twenty-four hours to one week after administration of the virus.

* * * * *